US009989485B2

(12) United States Patent
Popov et al.

(10) Patent No.: US 9,989,485 B2
(45) Date of Patent: Jun. 5, 2018

(54) METHOD FOR DETERMINING PORE VOLUME CHARACTERISTICS AND POROUS MATERIALS' MATRIX THERMAL CONDUCTIVITY

(75) Inventors: Yury Anatolievich Popov, Moscow (RU); Irina Olegovna Bayuk, Moscow (RU); Anton Vladimirovich Parshin, Ufa (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 534 days.

(21) Appl. No.: 14/411,419

(22) PCT Filed: Jun. 26, 2012

(86) PCT No.: PCT/RU2012/000509
§ 371 (c)(1),
(2), (4) Date: Feb. 26, 2015

(87) PCT Pub. No.: WO2014/003597
PCT Pub. Date: Jan. 3, 2014

(65) Prior Publication Data
US 2015/0168323 A1    Jun. 18, 2015

(51) Int. Cl.
*G01N 25/18*    (2006.01)
*G01N 15/08*    (2006.01)

(52) U.S. Cl.
CPC ............ *G01N 25/18* (2013.01); *G01N 15/08* (2013.01); *G01N 15/088* (2013.01)

(58) Field of Classification Search
CPC ........ G01N 25/18; G01N 27/18; G01N 30/66; G01N 2030/3015; G01N 2015/0833; G01N 15/082; G01N 30/30; G01K 1/16
(Continued)

(56) References Cited

U.S. PATENT DOCUMENTS 3,126,731 A * 3/1964 Armstrong ............ G01N 30/66
                                                     73/23.22
6,180,559 B1 * 1/2001 Roberts .................. B01J 23/02
                                                     423/608
(Continued)

FOREIGN PATENT DOCUMENTS

RU    1797026 A1    2/1993
RU    2334977 C2    9/2008
RU    2403561 C1    11/2010

OTHER PUBLICATIONS

Popov, et al., "Interrelations between thermal conductivity and other physical properties of rocks: experimental data", Pure Appl. Geophys., 160, 2003, pp. 1137-1161.
(Continued)

*Primary Examiner* — Gail Kaplan Verbitsky

(57) ABSTRACT

Prior to the measurements a first volume element is specified in a porous material sample in order to record the distribution of pore volume characteristics and matrix thermal conductivity along a surface of the porous material sample. A second volume element is set for the record of a thermal conductivity distribution along the surface of the sample with the dimensions equal or close to the dimensions of the first volume element for the record of the pore volume characteristics' and matrix thermal conductivity. The porous material sample is subsequently saturated with at least two fluids with known different thermal conductivities. After each saturation a sample thermal conductivity is measured in each volume element of the sample equal to the second volume element and pore volume characteristics and the porous material matrix thermal conductivity are determined for each volume element of the sample corresponding to the first volume element. The pore volume characteristics and the matrix thermal conductivity distribution along the surface of the sample are determined.

13 Claims, 2 Drawing Sheets

(58) Field of Classification Search
USPC ..... 374/44, 45, 100, 141, 29, 137, 110, 112, 374/53, 43
See application file for complete search history.

(56) References Cited

U.S. PATENT DOCUMENTS 8,560,265 B2 10/2013 Popov et al.
2008/0202220 A1 8/2008 Schmidt

OTHER PUBLICATIONS

Popov, et al., "Physical properties of rocks from the upper part of the Yaxcopoil-1 drill hole, Chicxulub crater", Meteoritics & Planetary Science 39, Nr 6, 2004, pp. 799-812.
Bayuk, et al., "Upper and lower stiffness bounds for porous anisotropic rocks", Geophysics Journal International, 175, 2008, pp. 1309-1320.
Bayuk, et al., "Identification of the fluid type in a reservoir rock", Journal of the Solid Earth 35, Nr. 11, 1999, pp. 917-923.

\* cited by examiner

METHOD FOR DETERMINING PORE
VOLUME CHARACTERISTICS AND
POROUS MATERIALS' MATRIX THERMAL
CONDUCTIVITY

TECHNICAL FIELD

The Invention is related to the field of studying physical properties of non-uniform porous materials, particularly—to the determination of the pore volume characteristics and these materials' matrix (space filled with a solid material only) thermal conductivity.

Non-uniform porous materials may include, for example, industrial materials, loose and consolidated rock samples, minerals.

BACKGROUND ART

A method for determination of pore volume characteristics and matrix thermal conductivity using sample thermal conductivity measurements saturated in series with three fluids with different thermal conductivity is known (Popov et al. Interrelations between thermal conductivity and other physical properties of rocks: experimental data. Pure Appl. Geophys., 160, 2003, p.p. 1137-1161). The method is based on the determination of a porous material sample porosity, matrix thermal conductivity and shape of the pores and cracks simulated using rotation ellipsoid and characterized by the same aspect ratio. The porous material sample porosity, matrix thermal conductivity and aspect ratio of the ellipsoids simulating pores and cracks are determined by solving a set of three nonlinear equations in three unknowns using thermal conductivity measurements on a porous material sample saturated in series with three fluids of a known different thermal conductivity. The equations in this set are equality values of theoretical and experimental thermal conductivity of the samples of a pore-fractured material saturated in series with three fluids of a known different thermal conductivity. The theoretical thermal conductivity values are determined using the known method of effective-medium theory autocorrelation which enables expressing a porous material thermal conductivity value depending on the thermal conductivity of the matrix, fluid filling the pores and cracks, porosity and the ellipsoids' aspect ratio. The porosity of the porous material sample, matrix thermal conductivity and aspect ratio of the ellipsoids simulating the pores and cracks are determined for the entire sample in total without considering these values' variations within the sample.

It is also known a method for determination of pore volume characteristics and matrix thermal conductivity (Popov et al. Physical properties of rocks from the upper part of the Yaxcopoil-1 drill hole, Chicxulub crater. Meteoritics & Planetary Science 39, Nr 6, 2004, p.p. 799-812), consisting in the successive saturation of a porous material sample with at least two fluids with the known different thermal conductivity and determination of the sample porosity. After each saturation of the porous material sample with the fluid the sample thermal conductivity is measured. Based on the cumulative results of thermal conductivity measurement on the porous material sample pore volume characteristics and porous material sample matrix thermal conductivity are determined by the known ratio. The known method provides for determination of the pore-fractured space and matrix thermal conductivity for the sample in general, which, in case of non-uniform samples results in the loss of critical information on the variability of the sample properties within the sample and does not provide the record of the porosity distribution which, given the sample non-uniformity, also results in the loss of important information on the sample properties.

The suggested method provides for the record of the pore volume characteristics' distribution within a sample, location of the sample zones with maximum and minimum pore volume characteristics' and matrix thermal conductivity values, determination of the sample porosity in certain zones of the sample. This detailed distribution of these characteristics enables locating weakened zones, non-uniformity zones in the sample. This, in its turn, enables judging, for example, of the most probable destruction zones within the porous material.

SUMMARY OF INVENTION

The method for determination of pore volume characteristics and matrix thermal conductivity comprises the following. Prior to the measurements a first volume element is specified in a porous material sample in order to record the distribution of the pore volume characteristics and matrix thermal conductivity along a surface of the porous material sample.

A second volume element is set for the record of a thermal conductivity distribution along the surface of the porous material with the dimensions equal or close to the dimensions of the first volume element for the record of the pore volume characteristics' and matrix thermal conductivity.

The porous material sample is subsequently saturated with at least two fluids with known different thermal conductivities.

After each saturation a sample thermal conductivity is measured in each volume element of the sample equal to the second volume element and pore volume characteristics and the porous material matrix thermal conductivity are determined for each volume element of the sample corresponding to the first volume element. The pore volume characteristics and the matrix thermal conductivity distribution along the surface of the sample are determined.

BRIEF DESCRIPTION OF THE DRAWINGS

The invention is explained by the drawings where.

DETAILED DESCRIPTION OF EMBODIMENTS

Figure 1:
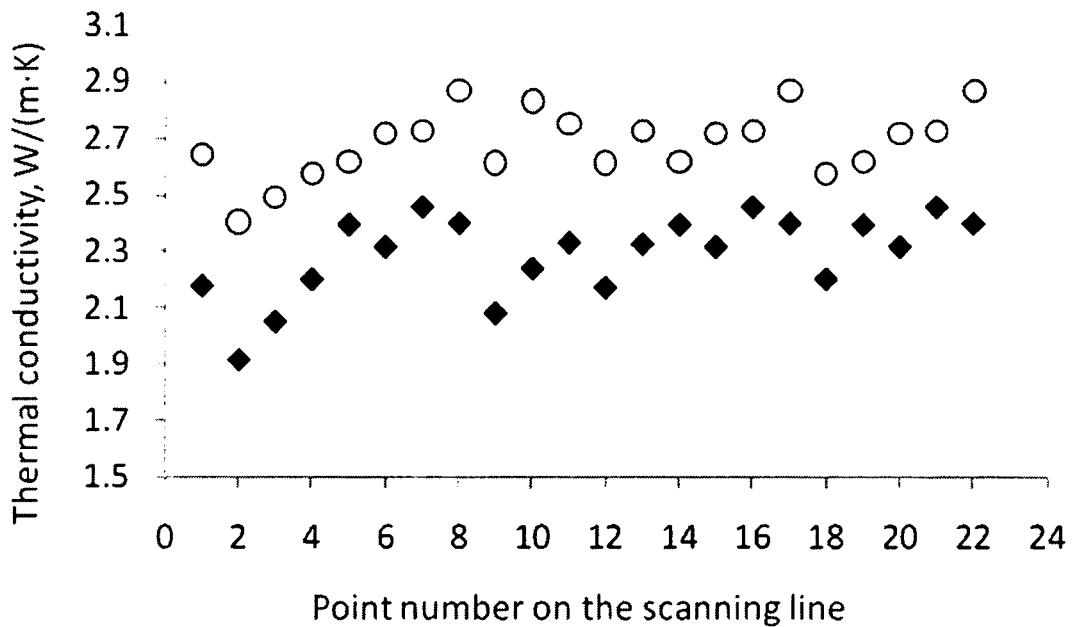
FIG. 1 shows the distribution of thermal conductivity of a dry- and water-saturated sample along the thermal conductivity measurement line,
FIG. 2—results of matrix thermal conductivity distribution,
FIG. 3—beta-distribution parameters' distribution results,
FIG. 4—an example of beta-distribution built for the parameters $\alpha=43$ and $\beta=4.4$ (porosity 7.6%).

The pore volume characteristics include porosity and geometrical parameters of a pore volume (for example, aspect ratio of ellipsoids simulating voids, parameters of a distribution function of the aspect ratio of the pores and fractures or any other values characterizing the shape of pores and fractures by their volume, attitude or size).

The first volume element dimensions—dimensions on the surface of the sample on which the thermal conductivity is measured, and the depth of the volume element in the sample are specified so as to ensure the required degree of the detailed distribution of the pore volume characteristics and matrix thermal conductivity along the surface of the porous material sample.

A second volume element should have dimensions equal to the dimensions of the first volume resolution element or close to these dimensions preferably, differing by maximum ±20% of its dimensions. To set the second volume element required parameters of the thermal conductivity measurement regime ensuring the second volume element are specified. The thermal conductivity measurement regimes may include the following parameters: a heating time, a heating power, a temperature record accuracy, time and duration of temperature measurements after the heating start etc.

The pore volume characteristics and matrix thermal conductivity for each first volume element of the porous material sample volume are determined so that the difference between theoretical and experimental thermal conductivity values obtained for the sample volume element during the saturation of the porous material with each fluid does not exceed the preset value.

The theoretical thermal conductivity value of the first volume element of the porous material sample is determined, depending on the porosity, pore volume geometry and matrix thermal conductivity, using the known ratio linking the porous material sample volume element thermal conductivity value with the values of the matrix porosity, geometry and thermal conductivity. For example, for this purpose known ratios of effective-medium theory methods (see below) may be used.

Suppose the thermal conductivity measurements are taken in a certain direction set in the main coordinate system by vector $n=(n_1, n_2, n_3)$. The main coordinate system shall be determined by symmetry elements of the porous material volume element, and in the main coordinate system effective thermal conductivity tensor is diagonal. Then in this direction the thermal conductivity value is determined using the known equation:

$$\lambda^{*(n)} = \lambda_{ij}^* n_i n_j = \lambda_{11}^* n_1^2 + \lambda_{22}^* n_2^2 + \lambda_{33}^* n_3^2, \quad (1)$$

Where $\lambda^*$ is the effective thermal conductivity tensor in the main coordinate system linked to porosity $\varphi$, pore volume geometry determined by tensor g, and matrix thermal conductivity tensor $\lambda^M$ as follows (Popov et al., Interrelations between thermal conductivity and other physical properties of rocks: experimental data. Pure Appl. Geophys., 160, 2003, pp. 1137-1161):

$$\lambda^* = [(1-\varphi) < \lambda^M(r)[I-g^M(\lambda^M(r)-\lambda^c)]^{-1} > + \varphi(\lambda^F(r)[I-g^F(\lambda^F(r)-\lambda^c)]^{-1} >] \times [(1-\varphi) < [I-g^M(\lambda^M(r)-\lambda^c)]^{-1} > + \varphi([I-g^F(\lambda^F(r)-\lambda^c)]^{-1} >]^{-1}. \quad (2)$$

In Equation (2) the angle brackets mean volume averaging which in case of statistically uniform medium, may be replaced by the ensemble statistical averaging. $\lambda^F(r)$ fluid thermal conductivity tensor in point r of the porous material volume element; I—unit matrix. Tensor g components look as follows $$g_{kl} = -\frac{1}{4\pi} \int n_{kl} \Lambda^{-1} d\Omega, \quad (3)$$

where $$n_{kl} = n_k n_l, \quad n_1 = \frac{1}{a_1}$$

$\sin \theta \cos \varphi,$ $$n_2 = \frac{1}{a_2}$$

$\sin \theta \sin \varphi,$ $$n_3 = \frac{1}{a_3}$$

$\cos \theta$, $d\Omega \equiv \sin \theta d\theta d\varphi$, and $a_i$ are semi-axes of the ellipsoids simulating mineral substance grains (M index), pores and fractures (F index); $\Lambda \equiv X_{ij}^c n_i n_j$, $\theta$ and $\varphi$ are polar and azimuth angles in the spherical coordinate system. $\lambda^c$ is reference body thermal conductivity tensor. Different selection of the reference body results in different effective-medium theory methods' equations, including autocorrelation method, providing $\lambda^c = \lambda^*$ (Popov et al. Interrelations between thermal conductivity and other physical properties of rocks: experimental data. Pure Appl. Geophys., 160, 2003, pp. 1137-1161), Hashin-Strickman method (Bayuk I., Gay J., Hooper J., and Chesnokov E. Upper and lower stiffness bounds for porous anisotropic rocks, Geophysics Journal International, 175, 2008, pp. 1309-1320), in which the reference body properties are supposed to be equal to those of the mineral substance or fluid depending on the rock internal structure. The reference body selection as $\lambda^c = (1-f) \lambda^M + f \lambda^F$, where f is a certain constant enables accounting for the pore volume cohesion degree (Bayuk I. and Chesnokov E. Identification of the fluid type in a reservoir rock, Journal of the Solid Earth 35, Nr. 11, 1999, pp. 917 923).

Determination of the pore volume porosity, geometry and matrix thermal conductivity for each element of the sample volume may be provided, for example, by minimizing the function characterizing the degree of deviation of the thermal conductivity theoretical values calculated by the matrix thermal conductivity values and pore volume characteristics using equations (2) and (3) from experimental thermal conductivity values obtained for the sample volume element in case of the sample saturation with each fluid.

This function may be represented as, for example, the sum of squares of deviations or the sum of modules of deviations of theoretical and experimental thermal conductivity values, hereby the summation is performed by the number of saturating fluids. Another example of the search for the solution for the pore volume porosity, geometry and matrix thermal conductivity is the accumulation of all the values of the pore volume porosity, geometry and matrix thermal conductivity which ensure the deviation between the theoretical and experimental values of the thermal conductivity obtained for the given sample volume element in case of the sample saturation with each fluid not exceeding a certain preset value, and subsequent calculation of the statistical characteristics of the accumulated values of the pore volume porosity, geometry and matrix thermal conductivity.

Then, by the results of the determination of the pore volume porosity, geometry and matrix thermal conductivity for each element of the sample volume the distribution of the pore volume porosity, geometry and matrix thermal conductivity along the surface of the porous material sample are found.

Different fluids, for example, air, oil, ethylene glycol or water may be used as fluids for the sample sequential saturation. Thermal conductivities of these fluids are well-known, stable and significantly different and makes, respectively, 0.024; 0.12; 0.27 and 0.60 W/(m·K). The saturation with each fluid is conducted so that the fluid completely filled the open fractures and pores.

In accordance with one of the embodiments before the measurements a minimum allowable thickness of the porous material sample which ensures thermal conductivity measurements with the preset accuracy with the first volume element in the porous material sample for the record of the pore volume distribution characteristics and matrix thermal conductivity is determined and a pore material sample has a thickness not less than the minimum allowable thickness.

In accordance with another possible embodiment the first volume resolution element in the porous material sample for the record of the distribution of the pore volume characteristics and matrix thermal conductivity along the porous material surface has a depth equal to the porous material sample thickness.

In accordance with yet another possible embodiment the porous material sample is made as a flat plate with a thickness equal to the double depth of the first volume element for the record of the distribution of the pore volume characteristics and matrix thermal conductivity for different points of the porous material surface. After each thermal conductivity measurement on the sample additional thermal conductivity measurements are taken on a sample opposite side to record a thermal conductivity distribution along the opposite side of the sample with the second volume element for the thermal conductivity distribution record. After that, using the results of the thermal conductivity distribution along the opposite side of the sample, distribution of pore volume characteristics and matrix thermal conductivity distribution along the opposite side of the porous material sample is determined. Therefore, based on the cumulative measurements on two opposite surfaces of the sample the distribution of the pore volume characteristics and matrix thermal conductivity along the entire volume of the porous material sample is recorded.

The porous material thermal conductivity measurements for different points of the surface of the porous material sample may be performed by heating the surface of the porous material sample with a heating spot moving at constant speed along different directions selected on the surface of the porous material sample and registering a temperature of a sample surface section using a temperature recording unit moving along a heating spot motion trajectory behind it with a speed equal to that of the heating spot.

To ensure a more reliable determination of the sample pore volume characteristics and matrix thermal conductivity, before measuring thermal conductivity, a maximum allowable temperature of the porous material sample heating and a permissible error of the porous material sample pore volume characteristics' and matrix thermal conductivity determination may be specified. The porous material sample is made with a thickness not less than a linear dimension of the first volume element for the porous material sample pore volume characteristics' and matrix thermal conductivity determination. Then the dimensions of the heating spot and of a heating temperature recording section on the sample surface, a heating spot movement speed, a lag distance between the temperature recording section and the heating spot along the heating spot motion trajectory, a time constant and a temperature resolution of the temperature recording unit are specified. These parameters are set to ensure the first volume element for the porous material pore volume characteristics' and matrix thermal conductivity determination, porous material sample heating temperature not exceeding the maximum allowable heating temperature of the porous material sample and the permissible error of the pore volume characteristics' and porous material matrix thermal conductivity determination.

In accordance with yet another embodiment, after the determination of the pore volume characteristics and matrix thermal conductivity distribution along the sample surface the layers of the porous material sample are sliced and after each slicing the sample is sequentially saturated with at least two fluids with the known different thermal conductivities. After each saturation a sample thermal conductivity in each volume element of the sample equal to the second volume element is measured, the pore volume characteristics and the porous material matrix thermal conductivity for each volume element of the sample corresponding to the first volume element are determined, and the pore volume characteristics and the matrix thermal conductivity distribution along the surface of the sample are determined. Based on the results of the pore volume characteristics' distribution along the porous material samples determination and the matrix thermal conductivity distribution along the porous material samples determination, the distribution of the pore volume characteristics in the entire volume of the porous material sample and distribution of the matrix thermal conductivity in the entire volume of the porous material sample are determined.

The method may additionally provide the determination of the distribution of at least one physical property with the first volume element for the record of the pore volume characteristics' and matrix thermal conductivity distribution along the surface of the porous material sample, and subsequent use of the results of at least one physical property distribution determination together with the results of the determination of the thermal conductivity to determine the distribution of the pore volume characteristics and matrix thermal conductivity along the surface of the porous materials' samples.

An additionally determined physical property of the porous material sample may be at least one property from the following group: an elastic waves speed, a sample electrical conductivity, a sample permeability, a sample density, a sample volumetric heat capacity.

The results of the determination of one or more additional physical properties of the porous material sample are used together with the results of the determination of thermal conductivity distribution in order to determine the pore volume characteristics and porous material sample matrix thermal conductivity. For this purpose in addition to Equations (1)-(3) linking the measured pore volume thermal conductivity and geometry, matrix porosity and thermal conductivity similar effective-medium theory ratios enabling linking the measured physical property with the pore volume geometry, pore volume porosity and relevant matrix physical properties are used. Hereby the equations for any effective transport property (electrical conductivity, dielectric and hydraulic permeability) are similar to equations (1)-(3) for effective thermal conductivity with the substitution of thermal conductivity tensor for electrical conductivity, dielectric or hydraulic permeability tensor. If the elastic waves' speeds are measured, the equations linking with the pore volume characteristics and matrix thermal conductivity look as follows. If the elastic waves' speed is measured in a certain direction set in the main coordinate system by vector $n=(n_1, n_2, n_3)$, then in this directions the elastic waves' speed values are determined via density and effective elasticity tensor using the known Green-Christoffel equation:

$$det(\Gamma_{ik}-\rho(v^{(n)})^2\delta_{ik})=0, \quad (4)$$

where $$\Gamma_{ik}=C_{ijkl}{}^{*}n_j n_l. \quad (5)$$

In equations (4) and (5) $v^{(n)}$ is the speed of a compressional or transversal wave in the direction n, $\rho$—density, $\delta_{ik}$—Kronecker delta, $C_{ijkl}{}^{*}$—elasticity effective tensor components. The elasticity effective tensor is determined by the equation similar to equation (2) in claim 1 description with the substitution of thermal conductivity tensors for elasticity tensors, second rank unit tensor for fourth rank unit tensor, second rank g tensor for fourth rank g tensor looking as follows $$g_{kmln} = \tilde{a}_{k)(l,n)(m} \equiv \frac{1}{4}(a_{klmn} + a_{mlnk} + a_{knlm} + a_{mnlk}), \quad (6)$$

$$\tilde{a}_{kmln} = \frac{1}{4\pi}\int n_{mn}\Lambda_{kl}^{-1}\sin\theta d\theta d\varphi,$$

$$\Lambda_{kl} \equiv C^*_{kmln}n_{mn},$$

$$n_{mn} \equiv n_m n_m,$$

$$n_1 = \frac{1}{a_1}\sin\theta\cos\varphi,$$

$$n_2 = \frac{1}{a_2}\sin\theta\sin\varphi,$$

$$n_3 = \frac{1}{a_3}\cos\theta.$$

If volumetric heat capacity or porosity along different directions selected on the porous material surface is measured, the relationships between their measured values and respective values of the matrix, saturating fluid and porosity look as follows $$(c\rho)^{(n)}=(c\rho)^*=(1-\varphi)(c\rho)^M+\varphi(c\rho)^F, \quad (7)$$

$$(\rho)^{(n)}=(\rho)^*=(1-\varphi)(\rho)^M+\varphi(\rho)^F, \quad (8)$$

Hereby the volumetric heat capacity and density do not depend on the direction even for a material with anisotropic elastic and transport properties do not depend on the pore volume geometry.

Determination of the pore volume porosity, geometry and matrix thermal conductivity for each element of the porous material sample volume may be provided, for example, by minimizing the function simultaneously characterizing the degree of deviation of the thermal conductivity theoretical values calculated by the matrix thermal conductivity values and other measured physical properties from the experimental values of thermal conductivity and other measured physical values obtained for the given sample volume element in case of the sample saturation with fluid. This function may be represented as, for example, the sum of squares of relative deviations or the sum of modules of relative deviations of theoretical and experimental values of thermal conductivity and other physical values, hereby the summation is performed by the number of saturating fluids. Another example of the search for the solution for the pore volume porosity, geometry and matrix thermal conductivity for the porous material sample volume element is the accumulation of all the values of the pore volume porosity, geometry and matrix thermal conductivity which ensure the deviation between the theoretical and experimental values of the thermal conductivity and other physical values obtained for the given sample volume element in case of the sample saturation with each fluid not exceeding a certain preset value, and subsequent calculation of the statistical characteristics of the accumulated values of the pore volume porosity, geometry and matrix thermal conductivity As an example of the embodiment let us consider pore volume characteristics and matrix thermal conductivity determination for a carbonate reservoir core sample with the diameter of 12 cm and length of 26 cm. The core sample is cut along its axis into two equal parts (semi-cylinders). One core part is used to measure thermal conductivity. The dimensions of the required first volume element are set for the determination of the pore volume characteristics and matrix thermal conductivity—an area with the diameter of 10×10 mm on the sample surface on which thermal conductivity measurements are performed and 20 mm deep into the sample. Then on the flat surface of the core sample holes with the diameter of 2 mm and depth of 20 mm are drilled perpendicular to the surface. The holes are drilled with 10-mm intervals along the lines on the sample surface parallel to each other at the distance of 10 mm. After that the porous material sample is extracted and dried for 12 hours at 100° C. Then the dry sample (i.e. in case of the pores and fractures filled with air) is prepared for thermal conductivity measurements using cylindrical probe method. The cylindrical probe method provides immersion of a hollow needle into the porous material sample. Inside the needle, along its length a thin heater and a temperature transducer are located. Before the measurements the time during which the sample is heated with the probe is set at 80 sec and the probe temperature record time interval is set at 60-80 sec which ensures volume resolution element during the record of the thermal conductivity distribution on the 10×10-mm diameter and 20-mm deep area on the sample surface on which core thermal conductivity is measured. Then the core thermal conductivity measurements are taken, to do this the probe is sequentially immersed into each of the holes drilled, the probe is heated at the constant heating power for 80 sec, the probe temperature is recorded with the time interval of 60-80 sec and temperature measurement results the thermal conductivity values are determined for the measurements in each of the holes. Then the same semi-cylindrical core sample is water-saturated in a vacuum unit which corresponds to the pores' and cracks' filling with the second fluid—water, instead of the previous fluid—air. Air thermal conductivity in atmospheric conditions is 0.024 W/(m·K), water thermal conductivity is 0.60 W/(m·K).

The vacuum unit is used to attain complete water saturation of the interconnected cracks and pores. Then thermal conductivity is measured in the water-saturated core in the same holes that were used for the dry core. The dry- and water-saturated core measurements for each element along each volume element along the scanning path result in obtaining two thermal conductivity values for the dry- and water-saturated core conditions (FIG. 1). To improve the pore volume characteristics' and matrix thermal conductivity determination the core saturation with a third fluid, for example, oil, is used, after which the thermal conductivity profiles are recorded again along the same 14 scanning lines on the oil-saturated core.

The thermal conductivity values obtained are used to determine the pore volume geometry, matrix porosity and thermal conductivity. The shape of the cracks and pores on which g value in equation (3) depends is simulated by the rotation ellipsoids characterized by the aspect ratio κ. In this case it is convenient to use depolarization factor D, linked with the aspect ratio by the equation $D=0.5(1-D_3)$. For oblong ellipsoids with the aspect ratio of κ, larger than 1, the relationship $$D_3 = (1-e^2)\frac{Arth(e)-e}{e^3}, e = \sqrt{\frac{\kappa^2-1}{\kappa^2}},$$

is valid, whereas for oblate ellipsoids with the aspect ratio κ, smaller than or equal to 1, $$D_3 = (1+e^2)\frac{e-arctg(e)}{e^3}, e = \left[\frac{1-\kappa^2}{\kappa^2}\right]^{0.5}.$$

The distribution of the cracks' and pores' volume on depolarization factor is described by two-parameter beta-distribution $$P(F) = \frac{\Gamma(\alpha+\beta)}{\Gamma(\alpha)\Gamma(\beta)}F^{\alpha-1}(1-F)^{\beta-1},$$

where Γ is gamma-function. Beta-distribution parameters α and β are non-negative and considered as unknown. Whereas the rock is isotropic the cracks' and pores' attitude is considered as chaotic.

Figure 2:
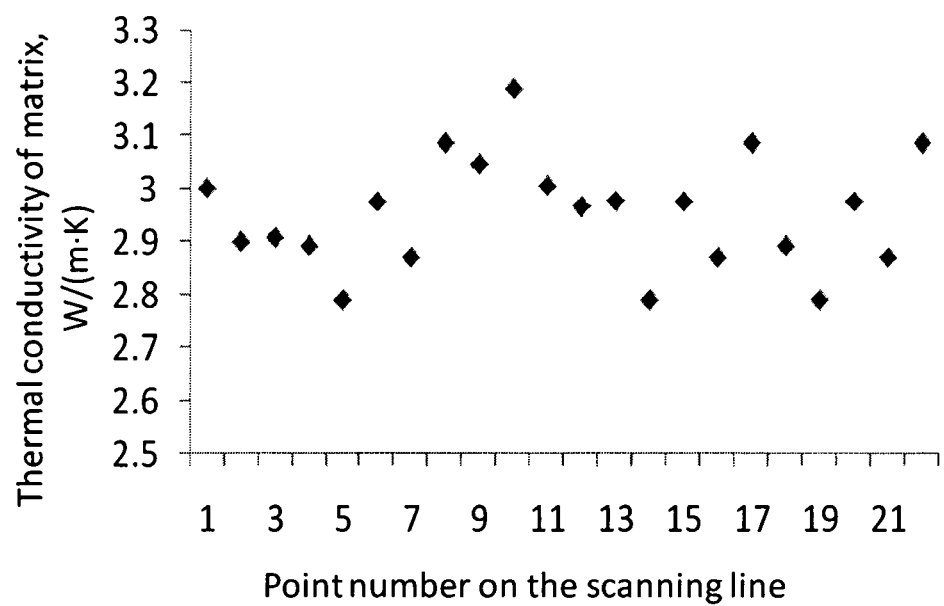
Figure 3:
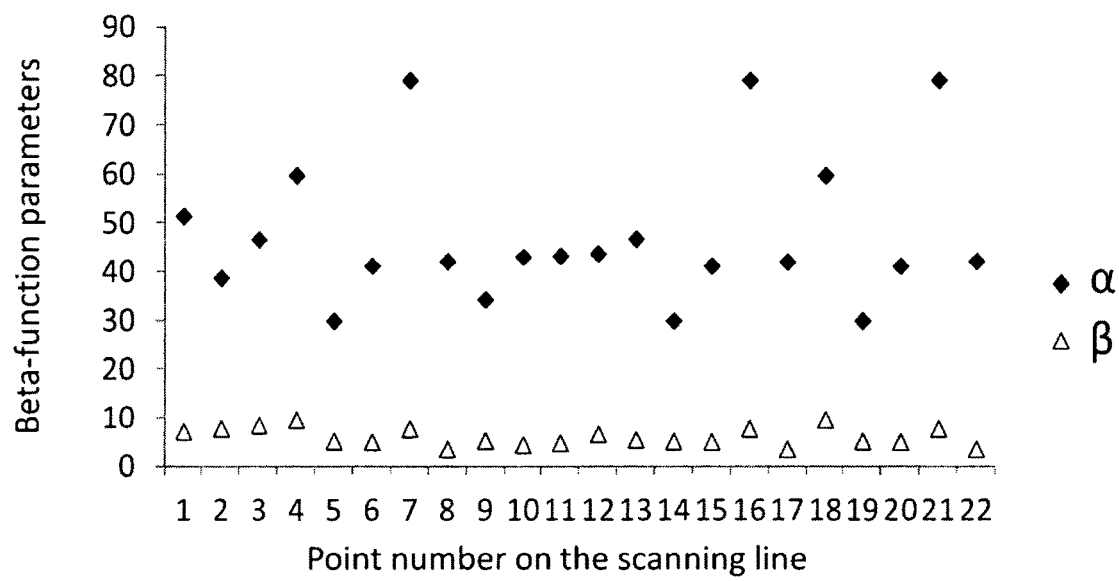
Figure 4:
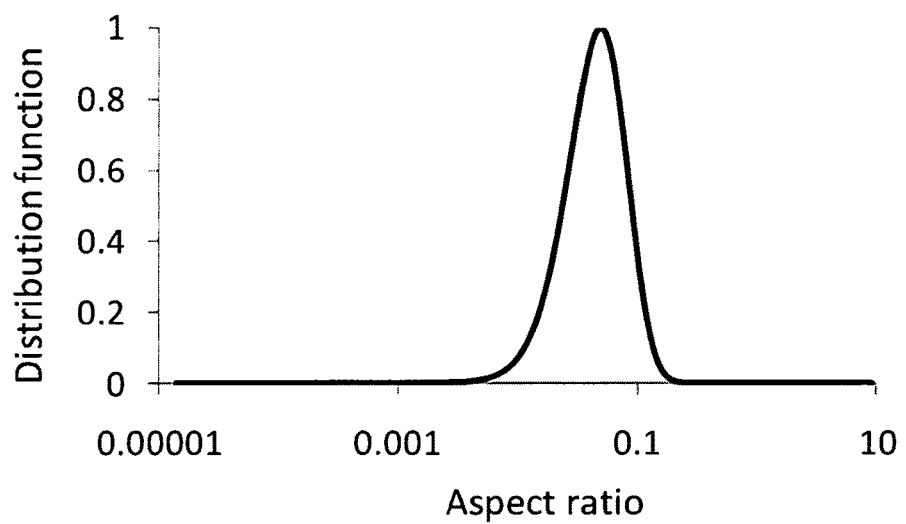

The unknown values in equation (2) are two beta-distribution parameters, matrix thermal conductivity and open porosity. To find the solution the potential change domains of each unknown value are set. For each of beta-distribution parameters is the interval [0.0001; 100]. The porosity may vary from 0.1 to 40%. The matrix thermal conductivity differs from the thermal conductivity determined using mineral composition because a carbonate collector may include disconnected pores as well as organic matter debris and capillary water. The matrix thermal conductivity variation is set in the range of its possible values 2.5-3.5 W/(m·K). The unknown beta-distribution parameters, matrix thermal conductivity and open porosity are determined by minimization of the sum of relative residuals of the theoretical and experimental values of thermal conductivity obtained for each saturating fluid. For the minimization a version of the deformed polyhedron method enabling accounting for the domain of the change of possible values for the parameters in question is used. FIG. 2-4 shows the solution for these values obtained for the scanning line on which the measurements in FIG. 1 were performed.

Preliminary determination of the minimum allowable thickness of the porous material sample ensuring thermal conductivity with the preset accuracy with the specified first volume element in the porous material sample for the record of the distribution of the pore volume characteristics and matrix thermal conductivity is possible. The minimum allowable thickness of the porous material is selected equal to the depth of the first volume element. Thus in the previous case of the embodiment the depth of the first volume element for the determination of pore volume parameters and matrix thermal conductivity is 20 mm. After that a 25-mm thick porous material sample is made which is thicker than 20 mm.

The porous material sample may be made as a flat plate with the thickness equal to the double depth of the specified first volume element for the record of the pore volume characteristics' and matrix thermal conductivity distribution. For example, if the preset depth of the first volume element is 8 mm, the porous material sample is made as a 16-mm thick plate. All the steps of the method are performed on two opposite sides of the sample after which based on the results of the thermal conductivity distribution record along the first and second surfaces of the porous material sample the distribution of the pore volume characteristics along the first and the second surfaces of the porous material and the distribution of the matrix thermal conductivity along the first and the second surfaces of the porous material as well as along the entire volume of the porous material sample is determined.

The thermal conductivity measurements on the surface of the porous material sample with the preset dimensions of the volume 5×5 mm on the sample surface and 5 mm deep into the sample depth may be performed using optical scanning method. Hereby the porous material sample surface is heated with a heating spot moving along a direction selected on the porous material sample at a constant speed behind the heating spot. For this purpose a laser beam falling onto the porous material sample surface is used, hereby the sample is displaced relative to the laser beam at a constant speed. During heating the heating temperature of the porous material sample section surface is recorded, hereby a recording section is located behind the heating spot along the motion direction and its motion along the porous sample surface with the speed equal to that of the heating spot motion is ensured. This temperature recording is performed using an infrared temperature transducer built on an infrared pyroelectric detector. The measurement regime parameters are selected to ensure spatial resolution of the thermal conductivity with the thermal conductivity detection area size of 5×5 mm on the core surface and at the depth of 5 mm during the thermal conductivity profile record along the scanning line. It is ensured at the following measurement regime parameters: scanning speed is 4 mm/sec, heating spot diameter is 3 mm, temperature record area diameter is 3 mm, distance between the heating spot centre and temperature record area centre on the core sample heated surface is 8 mm. These parameters set the volume resolution element—a semisphere with the diameter of 5 mm—for thermal conductivity distribution record. Moving the heating source and temperature transducer along the selected scanning path on the sample flat surface the temperature for each temperature recording section along the heating spot path is recorded and the temperature recorded is converted into the thermal conductivity value for each section along the temperature recording section motion line. Using this procedure core thermal conductivity in the points along the path is determined and thermal conductivity profile along the scanning path is recorded. This profiling operation is repeated for 13 scanning lines more selected on the carbonate reservoir core sample surface, these lines should be parallel to the first scanning line and the interval between each of them and the first scanning line should be 5 mm which is equal to the diameter of the pre-selected volume element. Such thermal conductivity measurements shall be performed for each saturated state of the porous material sample. Then based on the thermal conductivity measurement findings continuous distribution of the pore volume characteristics along different directions selected on the porous material sample surface and continuous matrix thermal conductivity distribution along the porous material sample is obtained.

Before the porous material sample thermal conductivity measurements maximum allowable heating temperature for the porous material sample which is determined as equal to 40° C., permissible error of the porous material matrix thermal conductivity measurement equal to 10% may be specified by the sample documents. After that a 10-mm thick porous material sample is made, 10 mm is larger than the linear dimension of the first volume element for the determination of the pore volume characteristics and porous material matrix thermal conductivity. Then, using calculated ratios, the same heating spot and the temperature recording section dimensions, a heating spot motion speed, a lag distance between the temperature recording section and the heating spot along the heating spot path as in the previous example, are set, but, additionally jointly the temperature recording unit resolution (0.02° C.) and effective power in the heating spot (0.8 W) are selected, which ensures maximum porous material sample temperature in the heating spot of max. 35° and pore volume characteristics' determination error of 10% and porous material matrix sample thermal conductivity of 8%, respectively.

As an embodiment of the method with the determination of the pore volume characteristics' and matrix thermal conductivity determination along the entire volume of the porous material sample a case may be provided when during the measurements on the carbonate reservoir core sample (diameter 12 cm and length 30 cm) all the steps including the sample fluid saturation and thermal conductivity determination along different directions selected on the sample surface are repeated. The first volume element for the pore volume characteristics' and matrix thermal conductivity determination is set so that its depth is 10 mm. Therefore, in case of measurements along different directions on the sample surface pore volume characteristics and matrix thermal conductivity for the 10-mm thick top layer of the porous material sample are determined. After that the sample is saturated with at least one more fluid and thermal conductivity measurements are repeated on the same surface, after which pore volume characteristics and matrix thermal conductivity for the first 10-mm thick layer are determined by the thermal conductivity measurement results. After that the sample is dried and a 10-mm thick layer is sliced off the top plane and the remaining core sample part thermal conductivity is measured using the previously applied method for the sample when it is saturated with two or more fluids. The thermal conductivity measurement regime parameters ensuring the specified second volume element for the record of the thermal conductivity distribution along different directions selected on the surface of the porous material sample are selected the same as for the first layer. Based on the results of the thermal conductivity determination along different directions selected on the sample surface, pore volume characteristics and matrix thermal conductivity for the sample second 10-mm thick layer, this is done similar to the way it was done for the first layer. After that the sample is dried again and one more 10-mm thick material layer is sliced off, after which the complete procedure of the thermal conductivity measurement and sample saturation is repeated, based on which pore volume characteristics and matrix thermal conductivity for the third 10-mm thick layer are determined. The layer slicing followed by the fluid saturation, thermal conductivity measurements and pore volume characteristics' and layers' matrix thermal conductivity determination is performed until the thermal conductivity measurement sample thickness is less than 10 mm. As a result, by the cumulative measurements' results a three-dimensional distribution of the pore volume geometry, porosity and thermal conductivity.

As another example of the embodiment let us again consider the case when for the measurements a carbonate reservoir core sample with the diameter of 12 cm and length of 30 cm is selected. All the steps including extraction, sample drying, its saturation with fluids and determination of thermal conductivity along different directions selected on the sample surface. For the same sample states during its saturation with different fluids for the same sections of the porous material sample surface in which thermal conductivity was measured, one more physical property of the porous material, for example, electrical conductivity is measured. The thermal conductivity and electrical conductivity values are used as cumulative values to determine the pore volume characteristics and matrix thermal conductivity. For this purpose known description ratios (1) (3) between thermal conductivity, electrical conductivity and pore volume geometry, matrix porosity and thermal conductivity are used.

Other properties from the group of properties may also measured—elastic wave speed, electrical conductivity, permeability, density, sample volumetric thermal conductivity—the sample elastic wave speed and permeability are measured. The measured values are used as cumulative data to determine the pore volume characteristics and matrix thermal conductivity.

The invention claimed is:

1. A method for determining pore volume characteristics and a porous materials' matrix thermal conductivity comprising:
   specifying a first volume element in a porous material sample for registering a distribution of pore volume characteristics and of a matrix thermal conductivity along a surface of the porous material sample,
   specifying a second volume element for registering a thermal conductivity distribution along the surface of the sample, the second volume element having dimensions equal or close to the dimensions of the first volume element,
   saturating the sample subsequently with at least two fluids with known different thermal conductivities,
   after each saturation measuring a sample thermal conductivity in each volume element of the sample equal to the second volume element and determining pore volume characteristics and the porous material matrix thermal conductivity for each volume element of the sample corresponding to the first volume element, and determining the pore volume characteristics and the matrix thermal conductivity distribution along the surface of the sample.

2. The method of claim 1, wherein the pore volume characteristics include a porosity and geometrical parameters of the pore volume.

3. The method of claim 2, wherein the geometrical parameters of the pore volume include aspect ratio of ellipsoids simulating voids, parameters of a distribution function of the aspect ratio of pores and fractures or any other values characterizing a shape of pores and fractures by their volume, attitude or size.

4. The method of claim 1, wherein the dimensions of the second volume element for registering the thermal conductivity distribution along the surface of the sample differ from the dimensions of the first volume resolution element for registering the distribution of the pore volume characteristics' and of the matrix thermal conductivity distribution by not more than 20%.

5. The method of claim 1 wherein sample saturation fluids are selected from a group consisting of ethylene glycol, oil and water.

6. The method of claim 1 wherein the first volume element for registering the distribution of the pore volume characteristics' and of the matrix thermal conductivity along the surface of the sample has a depth equal to a thickness of the porous material sample.

7. The method of claim 1 wherein the porous material sample has a thickness not less than a minimum allowable thickness ensuring thermal conductivity measurements with the given accuracy for the first volume element for registering a distribution of the pore volume characteristics and of the matrix thermal conductivity along the surface of the sample.

8. The method of claim 1 wherein the sample is made as a flat plate with a thickness equal to the double depth of the first volume element for registering distribution of the pore volume characteristics' and of the matrix thermal conductivity, after each measurement of the thermal conductivity additional measurements are performed on the opposite side of the sample surface in order to record the thermal conductivity distribution along the opposite side of the sample with the second volume element for registering the thermal conductivity distribution, after that the distribution of the pore volume characteristics' and of the matrix thermal conductivity along the sample's two surfaces and the distribution of the matrix thermal conductivity and pore volume characteristics in the entire volume of the sample are determined.

9. A method of claim 1 wherein the porous material sample thermal conductivity measurements for different points on the porous material sample surface are performed by heating the porous material sample surface with a heating spot moving at a constant speed along different directions selected on the surface of the porous material sample surface, registering a temperature of the sample surface by a temperature recording unit moving along the heating spot path behind it at the same speed as the heating spot and subsequent determination of the thermal conductivity distribution along the heating spot path.

10. A method of claim 9 wherein before the thermal conductivity measurements a maximum allowable heating temperature of the sample and a permissible error of the pore volume characteristics' and the porous material sample matrix thermal conductivity determination are specified, the porous material has a thickness not less than a linear dimension of the first volume element for the determination of the pore volume characteristics and the porous material sample matrix thermal conductivity, the heating spot and a heating temperature recording section on the sample surface dimensions, the heating spot movement speed, a lag distance between the temperature recording section and the heating spot along the heating spot path, a time constant and a temperature resolution of the temperature recording unit are specified so as to provide the specified first volume element, the porous material sample heating temperature not exceeding the maximum allowable heating temperature of the sample and the permissible error of the pore volume characteristics' and the porous material sample matrix thermal conductivity.

11. A method of claim 1 wherein after the determination of the pore volume characteristics' distribution and matrix thermal conductivity distribution along the porous material sample surface:

porous material sample layers are sliced sequentially, after each layer slicing the porous material sample is sequentially saturated with at least two fluids with the known different thermal conductivities, after each saturation a sample thermal conductivity in each volume element of the sample equal to the second volume element is measured, the pore volume characteristics and the porous material matrix thermal conductivity for each volume element of the sample corresponding to the first volume element are determined, and the pore volume characteristics and the matrix thermal conductivity distribution along the surface of the sample are determined, and based on the results of the pore volume characteristics' and the matrix thermal conductivity distribution determination along the surface of the sample, the distribution of the pore volume characteristics of the matrix thermal conductivity in entire volume of the porous material sample are determined.

12. A method of claim 1 wherein additionally a distribution of at least one sample physical property with the specified first volume element for the record of the pore volume characteristics' and matrix thermal conductivity along the surface of the porous material sample is determined, and the results of at least one sample physical property distribution determination are used together with the results of the thermal conductivity distribution determination for the determination of the distribution of the pore volume characteristics' and matrix thermal conductivity distribution along the surface of the porous materials' samples.

13. A method of claim 12 wherein the additionally determined physical property of the porous material sample is selected from a group consisting of an elastic waves speed, a sample electrical conductivity, a sample permeability, a sample density, a sample volumetric heat capacity.

* * * * *